United States Patent [19]

Narisawa et al.

[11] 4,187,377
[45] Feb. 5, 1980

[54] HALOGEN-CONTAINING S-TRIAZINE COMPOUND

[75] Inventors: Shigeyuki Narisawa; Shohei Yoshida; Hiroshi Kawahara, all of Yokohama, Japan

[73] Assignee: Asahi Glass Company, Ltd., Tokyo, Japan

[21] Appl. No.: 807,636

[22] Filed: Jun. 17, 1977

[51] Int. Cl.$^2$ ............................................ C07D 251/30
[52] U.S. Cl. .......................... 544/219; 260/45.8 NT; 252/8.1; 8/190; 106/15 FP; 117/136; 428/921; 106/15.05
[58] Field of Search ........................................ 544/219

[56] References Cited
U.S. PATENT DOCUMENTS

| | | | |
|---|---|---|---|
| 3,206,407 | 9/1965 | Lutwack | 544/219 |
| 3,240,749 | 3/1966 | Dexter et al. | 544/219 |
| 3,700,666 | 10/1972 | Robin et al. | 544/219 |
| 3,729,471 | 4/1973 | Robin et al. | 544/219 |
| 3,816,417 | 6/1974 | Economy et al. | 544/219 |
| 3,847,915 | 11/1974 | Bishop et al. | 544/219 |
| 3,978,028 | 8/1976 | Sundermann et al. | 544/219 |
| 4,039,538 | 8/1977 | Klinkenberg et al. | 544/219 |

*Primary Examiner*—John M. Ford
*Attorney, Agent, or Firm*—Oblon, Fisher, Spivak, McClelland & Maier

[57] ABSTRACT

Halogen-containing s-triazine compounds having two or more s-triazine rings which are remarkably useful as flame retardants are disclosed.

The compounds can be produced by reacting cyanuric chloride with a specific phenol and a specific bisphenol in the presence of a base in a solvent.

6 Claims, No Drawings

HALOGEN-CONTAINING S-TRIAZINE COMPOUND

BACKGROUND OF THE INVENTION:

1. Field of the Invention:

The present invention relates to a novel halogen-containing s-triazine compounds having two or more s-triazine rings. More particularly, it relates to the use of the compounds and the preparation of the compounds. The s-triazine means 1,3,5-triazine in the specification.

2. Description of the Prior Art:

Organic compounds having high content of halogen atoms have been used as flame retardants for synthetic resins, synthetic fibers or other materials.

The synthetic resins of hydrocarbon type polymers are normally flammable. Accordingly, a flame retarding treatment is preferably applied and in some field, the flame retarding treatment is indispensable.

It has been known for the flame retarding treatment of synthetic resins to use halogen-containing compounds, phosphorus-containing compounds, antimony compounds, nitrogen-containing compounds etc. The halogen-containing compounds have been especially effective. The flame retarding property is higher depending upon increase of halogen content in the halogen-containing compounds. However, it is not always effective as the flame retardants to have high halogen content. It is important to have various physical and chemical characteristics such as high miscibility to the synthetic resin and suitable melting point and high thermal stability and high weather-proofing property and not to deteriorate the synthetic resin etc.

It has been known to use halogen-containing s-triazine compounds having single s-triazine ring as flame retardants. For example, tris-(2,4,6-tribromophenoxy)-s-triazines have been disclosed in French Pat. No. 1,566,675 published on May 9, 1969 and tris-(polybromophenoxy)-s-triazines as flame retardants for polystyrenes and polyolefins have been disclosed in U.S. Pat. No. 3,843,650 and published on Oct. 22, 1974, and tris-(polyhalophenoxy)-s-triazines as flame retardants for polyolefins, polystyrenes, ABS, PVC etc., have been disclosed in Japanese Unexamined Patent Publication No. 25232/1972 published on Oct. 19, 1972.

These tris-(polyhalophenoxy)-s-triazines have high flame retardancy, however, they have not enough thermal stability and they cause bleed-out when they are blended to the synthetic resins.

SUMMARY OF THE INVENTION:

It is an object of the present invention to provide halogen-containing s-triazine compounds having two or more s-triazine rings.

It is another object of the present invention to provide new use of halogen-containing s-triazine compounds having two or more s-triazine rings as flame retardants which have high thermal stability and do not cause bleed-out when they are blended to synthetic resins.

It is the other object of the present invention to provide a process for producing the halogen-containing s-triazine compound having two or more s-triazine rings.

The novel halogen-containing s-triazine compounds having two or more s-triazine rings of the present invention are the compounds having the formula

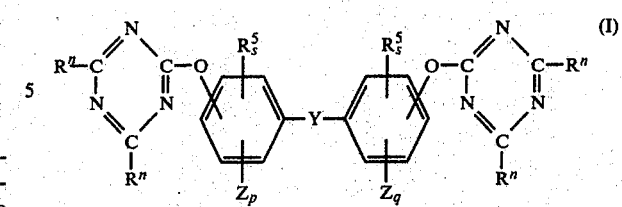

wherein $R^n$: OH, $R^1$, $R^2$ or $R^3$;

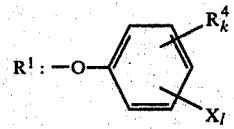

$R^4$: a lower alkyl group or a lower haloalkyl group;
X: Br or Cl
k,l: 0 or an integer of 1 to 5;
$k+l \leq 5$

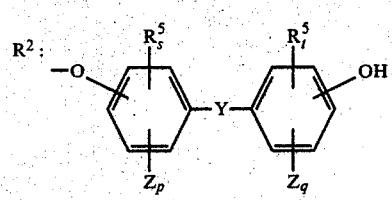

$R^5$: a lower alkyl group or a lower haloalkyl group;
Z: Br or Cl
p,q: 0 or an integer of 1 to 4;
s,t: 0 or an integer of 1 to 4;
$p+q+s+t \leq 8$
$1+p+q \geq 2$
Y: a lower alkylene, a lower haloalkylene, alkylidene group, or —$SO_2$—, —SO—, —S—, —O—, —CO— or direct bond

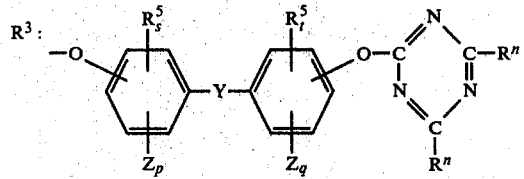

$R^n$, $R^5$, Z, Y, p, q, s, t: defined above.

The halogen-containing s-triazine compounds (I) are produced by reacting cyanuric chloride, a phenol having the formula

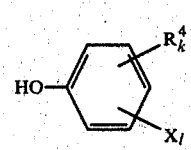

and a bisphenol having the formula

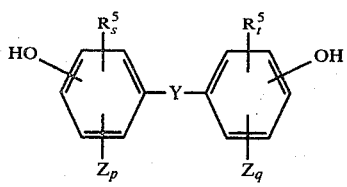

at a ratio of 3-2a mole of the phenol (II) and a mole of the bisphenol (III) per 1 mole of cyanuric chloride (0<a<3/2) in the presence of more than 3 equivalents of a base in a solvent.

DETAILED DESCRIPTION OF THE PREFERRED EMBODIMENTS:

The halogen-containing s-triazine compounds are briefly shown by the formula (I) though they are complicated reaction products. The compounds having various physical or chemical properties can be formed and they can be selected for blending them to synthetic resins as flame retardants depending upon the kind of the synthetic resin.

In the formula (I), when $R^n$ are respectively OH, $R^1$ or $R^2$, the compounds have two s-triazine rings. When $R^n$ is $R^3$, the compounds having more than two s-triazine rings. The number of s-triazine rings can be 2 to 20 or more. When the molecular weights of the compounds (I) are high, the polymers having the chain structure the net structure or the cyclic structure can be obtained. Certain compounds (I) are solvent insoluble polymers whose molecular weight can not be measured.

The compounds (I) comprises s-triazine rings, phenol group, bisphenol group.

The phenol group is shown as $R^1$ which is derived from phenols having the formula

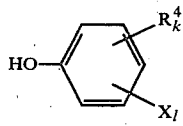

wherein $R^4$: a lower alkyl or a lower haloalkyl group ($C_1$–$C_3$); k: 0 or an integer of 1 to 5 preferably 0, 1, 2 or 3 (the content of $R^4$ is preferably lower because the halogen content in the phenol group is lowered by increasing the content of $R^4$); X: Br or Cl (a mixture of Br and Cl can be considered); l: 0 or an integer of 2 to 5 (it is preferable that l is 3 to 5 to be higher halogen content).

Suitable phenols (II) which derive $R^1$ include phenol, halophenols such as monobromophenol, monochlorophenol, dibromophenol dichlorophenol, tribromophenol, trichlorophenol, pentabromophenol, pentachlorophenol, cresol, monobromocresol, monochlorocresol, dibromocresol, dichlorocresol, tribromocresol, trichlorocresol, haloalkyl phenols such as dibromopropyl dibromophenol, dichloropropyl dichlorophenol etc.

It is especially preferable to use tribromophenol, trichlorophenol, pentabromophenol, pentachlorophenol. Two or more types of the phenol groups can be introduced in the compounds (I) by using two or more phenols (II).

The bisphenol group is shown as $R^2$ which is derived from bisphenols having the formula

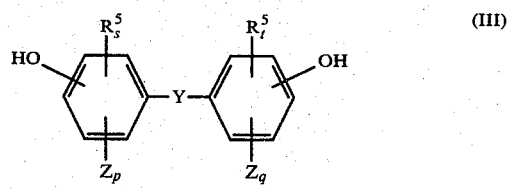

wherein $R^5$: a $C_1$–$C_3$ lower alkyl or a $C_1$–$C_3$ lower haloalkyl group; s, t: 0 or an integer of 1 to 4 preferably 0, 1 or 2 (it is preferable that s and t are respectively 0 to be higher halogen content); Z: Br or Cl (a mixture of Br and Cl can be considered); p, q: 0 or an integer of 1 to 4; preferably p=2 and q=2; Y: a $C_1$–$C_5$ lower alkylene, a lower $C_1$–$C_5$ haloalkylene, or a $C_1$–$C_5$ lower alkylidene group or —$SO_2$—, —SO—, —S—, —O—, —CO— or direct bond. The alkyl group, and the haloalkyl group and the alkylidene group have 1 to 5 preferably 1 to 3 carbon atoms.

It is preferable that Y is —$CH_2$—, —$C(CH_3)_2$—, —$SO_2$— especially —$C(CH_3)_2$—.

Suitable bisphenols (III) include

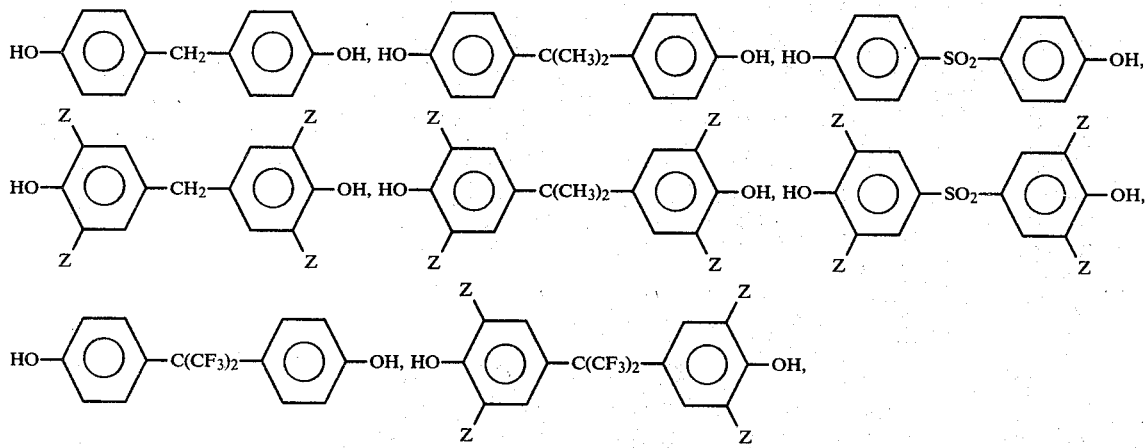

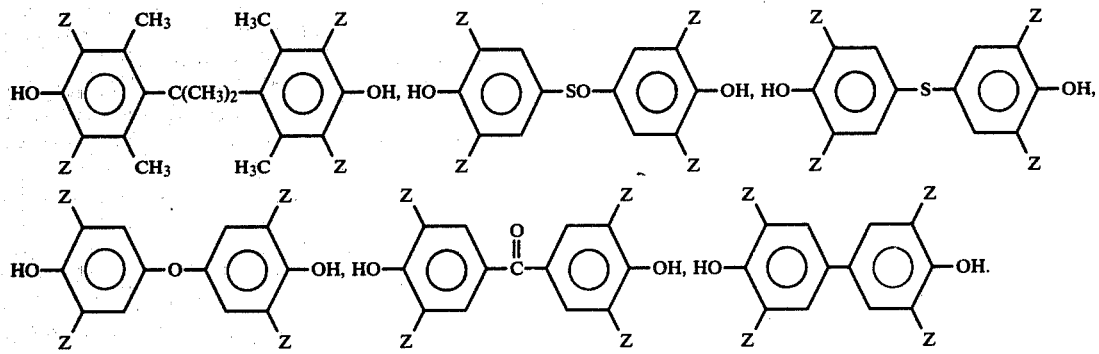

It is preferable to use the following bisphenols

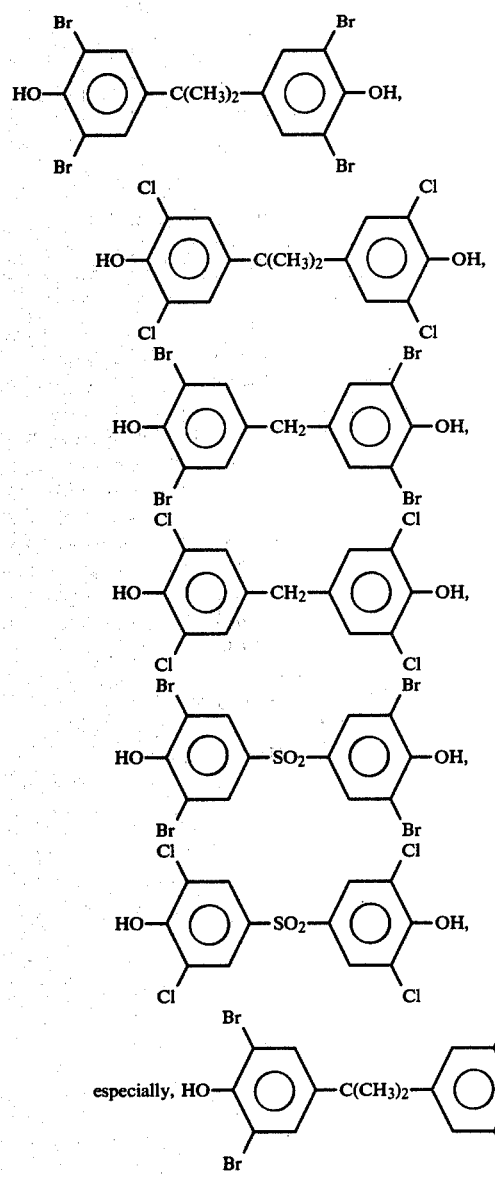

It is necessary that a total of l and p+q which relate to halogen content is 2 or more, but either of l or p+q can be zero. It is preferable that $l+p+q \geq 6$ especially $l=3$ to 5 and $p+q=4$.

The novel compounds (I) of the present invention have two or more s-triazine rings and bisphenol group. The most of the terminal groups are the phenol groups $R^1$ and are not so many OH or $R^2$ groups. Accordingly, the compounds (I) have only small number of OH groups. The heat stability of the compounds as the flame retardants is lowered by the presence of OH groups. In the novel compounds (I), it is preferable that the average number of OH is less than 0.5 per 1 molecule especially less than 0.2 per 1 molecule.

The novel compound (I) is normally a mixture having certain distribution of molecular weights as the same with the conventional condensation polymers, though it is possible to obtain the compound (I) having a specific molecular weight.

The condensation polymers having s-triazine rings and bisphenol groups have been disclosed in Journal of Polymer Science: Part A-1 Vol. 7 3089–3100 (1969). However, the known condensation polymers contain a halogen atom and are not effective as the flame retardant, but can be used as thermosettable resins.

The closest compounds are condensation polymers of triphenoxy-s-triazine (triphenylisocyanurate) and bisphenol A which are different from the compounds (I) because a halogen atom is not contained and one OH group is contained in one molecule.

The novel compounds (I) contain two or more s-triazine rings and usually 2 to 20 especially 2 to 10 of s-triazine rings. The compounds (I) having more than 20 of s-triazine rings can be prepared.

It is usual to obtain a mixture of the compounds (I) having a distribution of molecular weights. The molecular weight of the compound (I) is dependent upon the kind of halogen atoms and the halogen content and is usually more than 1,000. It is preferable to be more than 1,200 when the halogen content is high. It is preferable to be more than 1,500 when the halogen atoms are mostly bromine atom. When the halogen atoms are bromine atoms, it is possible to obtain the compound (I) having a molecular weight of more than 10,000.

The flame retardancy is higher when the halogen content is higher. It is preferable to have the bromine content of more than 30 wt.% especially more than 50 wt.% in the novel compound (I) to have excellent flame retardancy. It is preferable to have the chlorine content of more than 20 wt.% especially more than 40 wt.%. When the halogen atoms are both of bromine and chlorine atoms, the halogen content is preferably middle value. Since bromine atoms impart higher flame retardancy, it is preferable that all or more than half of halogen atoms are bromine atoms as the flame retardant.

The flame retardant of the compound (I) can be used by combining it with the other flame retardant. As described below, in some case, the compound (I) of the present invention is produced with a mixture of the compound (I) and the known triphenoxy-s-triazine compound such as tris-(polyhalophenoxy)-s-triazine. The mixture can be used without separating the compound (I) as the flame retardant. However, tris-(polyhalophenoxy)-s-triazine has relatively low thermal stability and may cause bleed-out whereby, the content of tris-(polyhalophenoxy)-s-triazine is preferably less than a half in the mixture.

The flame retardants of the compounds (I) are useful for imparting flame retardancy to synthetic resins, synthetic fibers, natural fibers, paper, wood etc., and especially useful for imparting flame retardancy to thermoplastic or thermosettable synthetic resins.

The synthetic resins include polyolefins such as polyethylene, polypropylene, polybutylene, polystyrene resins such as polystyrene, ABS, AS, polyacrylic resins such as polyacrylic acid esters, polymethacrylic acid esters, polyvinylacetate resins such as polyvinyl acetate, polyvinyl acetal, polyvinyl butyral, polyhalovinyl resins such as plasticized polyvinylchloride, polyvinylidene chloride, polyesters such as polyethyleneterephthalate, polypropyleneterephthalate, polybutyleneterephthalate, polyamide resins such as nylone 66, nylone 6, polycarbonate resins, polyurethane resins, polyether resins, or other thermplastic resins or unsaturated polyester resins, epoxy resins, vinyl ester resins, phenol resins, ally resins, melamine resins, silicone resins, and other thermosettable resins.

The flame retardants of the compounds (I) are also effective for imparting flame retardancy to semisynthetic resins and natural resins and synthetic fibers made of the synthetic resins and natural fibers such as cotton, hemp, wool etc. They are especially useful for imparting flame retardancy to thermoplastic polymers and copolymers produced by using a monomer having polymerizable unsaturated double bond and condensation polymers.

The synthetic resins or synthetic fibers can contain a reinforcing material such as glass fiber, a filler, a ultraviolet ray stabilizer, a thermal stabilizer, an antioxidant, a lubricant, a pigment etc.

One of the characteristics of the flame retardants of the present invention is to have high thermal stability (heat resistance).

The conventional halogen-containing flame retardants especially bromine-containing flame retardants have disadvantage to emit bromine and to color the flame retardant or the synthetic resin containing the flame retardant.

The flame retardants of the present invention have high stability in a molding operation and are not decomposed. Even though the thermoplastic resins containing the flame retardant of the present invention are molded or processed by an injection molding, an extrusion molding etc. in the molten condition, the resins are not colored. The stability of the flame retardants of the present invention is excellent whereby the weather resistance is also excellent.

The flame-retardants of the present invention have relatively high melting point and have high affinity to the synthetic resins, the bleed-out of the flame retardant from the synthetic resin is not found.

The flame retardants of the present invention have relatively high molecular weight, whereby the flame retardants have advantage that the mechanical strength or thermal deforming temperature of the synthetic resins are not highly decreased when they are blended to the synthetic resins. Moreover, the molecular weight, the OH group content and the halogen content of the flame retardants of the present invention can be easily controlled by selecting the ratio of the starting materials and the reaction conditions whereby it is possible to give the melting point close to that of the synthetic resin or to control affinity to the synthetic resin to give effective flame retardant.

The flame retardant of the invention can be use without an addition of the other agent. However, it is preferable to combine it with an auxiliary agent such as antimony compounds such as antimony trioxide, antimony halides and other metal compounds such as zinc oxide, bismuth oxide etc. It is especially effective to combine the antimony compound such as antimony trioxide, antimonates, antimonites antimonous acid esters, etc.

The flame retardants of the present invention can be used together with the other flame retardant such as halogen-containing compounds, phosphorus-containing compounds, nitrogen-containing compounds, and metal compounds. Synergistic effect of flame retardancy can be expect by combining the flame retardant of the present invention and the phosphorus-containing compound or the halogen-phosphorus-containing compound.

The amount of the flame retardant of the present invention to the synthetic resin is not critical when the flame retardant of the present invention is used without any other flame retardant, the amount of the flame retardant is preferably 5 to 40 wt.% to the synthetic resin. When the auxiliary agent such as antimony trioxide or the other flame retardant is combined, the amount of the flame retardant of the present invention is preferably 1 to 30 wt.%.

The novel compounds (I) used as the flame retardant can be prepared by various methods.

It is possible to use trichloro-s-triazine (cyanuric chloride), 2-phenoxy-4,6-dichloro-s-triazine, 2-polyhalophenoxy-4,6-dichloro-s-triazine as the starting materials for introducing s-triazine ring. Thus, cyanuric chloride is preferably used from the viewpoint of the cost. The phenols (II) and the bisphenols (III) are respectively used for introducing the phenol group and the bisphenol group.

The halogen-containing s-triazine compound (I) is preferably produced by reacting cyanuric chloride, a phenol having the formula

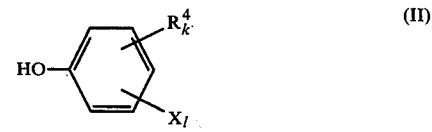
(II)

and a bisphenol having the formula

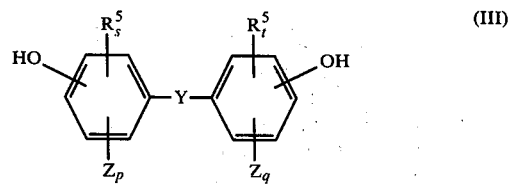
(III)

at a ratio of 3-2a mole of the halophenol (II) and a mole of the bisphenol (III) per 1 mole of cyanuric chloride ($0<a<3/2$) in the presence of more than 3 equivalents of a base in a solvent.

In the case of $0<a<\frac{1}{2}$, the known triphenoxy-s-triazines having three of

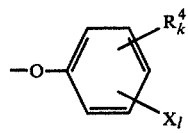

on the s-triazine ring or the halo derivatives thereof are produced as by-products to obtain the reaction mixture of the halogen-containing s-triazine compound (I) and the by-product. The mixture can be also used as the flame retardant whereby it is not necessary to separate the by-product.

In order to obtain only the halogen-containing s-triazine compound (I), the ratio of the starting materials is in the range of $\frac{1}{2} \leqq a < 3/2$.

It is preferable to produce the compound (I) in the range of $\frac{1}{2} \leqq a < 3/2$.

In the reaction, various bases can be used. It is preferable to use a water soluble base in a form of an aqueous solution.

Suitable bases include alkali metal hydroxides, salts thereof and alkaline earth metal hydroxides such as sodium hydroxide, potassium hydroxide, calcium hydroxide, sodium carbonate, sodium bicarbonate etc. It is preferable to use an aqueous solution of sodium hydroxide.

In the reaction, various solvents can be used. It is preferable to use an organic solvent or a mixture of an organic solvent and water.

Suitable organic solvents include hydrocarbons, halohydrocarbons, nitrohydrocarbons, ethers, cyclic ethers, ketones, esters, alcohols and other solvents such as heptane, cyclohexene, benzene, xylene, toluene, methylenechloride, chloroform, carbon tetrachloride, tetrachloroethylene, monochlorobenzene, nitrobenzene, n-butyl ether, cellosolve, 1,4-dioxane, tetrahydrofuran, acetone, methylethyl ketone, etc. It is possible to use two or more kinds of the solvents or to mix the solvent with the other solvent.

When only organic solvent is used as the solvent, it is preferable to use cyclic ethers such as 1,4-dioxane, tetrahydrofuran, ketones such as acetone, methylethyl ketone, halohydrocarbons such as monochlorobenzene and nitrohydrocarbons such as nitrobenzene etc.

When only the organic solvent is used, cyanuric chloride, the phenol (II) and the bisphenol (III) are added to the organic solvent and the base is added to the mixture with stirring. The reaction temperature is preferably lower than 40° C. especially lower than 20° C. When the temperature of the mixture in the addition of the base is too high and an aqueous solution of the base is added, it causes to increase the number of OH groups in the resulting halogen-containing s-triazine compound. It is considered to form OH groups bonded to the s-triazine rings by reacting cyanuric chloride with water of the aqueous solution of the base. When the OH content is high, the flame retardancy of the product is lowered. When the reaction temperature at the addition of the base is lower than 40° C., the tendency increasing the OH content is negligible. After the addition of the aqueous solution of the base, the reaction temperature is not limited to lower than 40° C.

The reaction can be carried out in the absence of a catalyst, but it can be accelerated by using a catalyst such as an organic acid metal salt, an inorganic metal compound or a quaternary ammonium salt. After the addition of the base, the reaction is performed for the specific time and then, if necessary the reaction is accelerated and the aging of the reaction product is attained by rising the temperature. After the reaction, the reaction product is post-treated by a filtration, a washing and a drying to obtain the product. The product is usually insoluble in the solvent. However, when a part or whole of the product is dissolved in the solvent, it is possible to precipitate the product by adding the solution to a precipitating agent such as water, or methanol. The resulting product is usually white powder and the yield can be more than 80%.

It is possible to employ the multi-step method. For example, it is possible to react cyanuric acid with the bisphenol (III) and then, to react the phenol (II). It is also possible to react cyanuric chloride with the bisphenol (III) and then, to react a mixture of the phenol (II) and cyanuric chloride and/or the bisphenol (III). The halogen-containing s-triazine compound (I) having desired structure can be obtained by these methods.

When the halogen-containing s-triazine compound (I) is produced by using only the organic solvent which can be azeotropically distillated with water and an aqueous solution of a base such as NaOH is used, the organic solvent is azeotropically distilled with water. The separation of water from the organic solvent is difficult and the recycling of only the organic solvent is difficult. Even though water can be removed by using a dehydrating agent, it is disadvantageous because of high cost. It is considered to be advantageous if a mixture of water and the organic solvent can be used as the solvent. When the halogen-containing s-triazine compound (I) is produced by using a mixture of water and the organic solvent, the tendency to increase the number of OH groups in the compound (I) has been found. It is not preferable to increase the number of OH groups because of lowering the flame retardancy. In accordance with the study of the reason why the number of OH groups is increased, it has been found that when cyanuric chloride contacts with water for a long time, hydrolysis of cyanuric chloride is caused to form OH groups which are directly bonded on the s-triazine ring.

The inventors have been studied to produce the halogen-containing s-triazine compound having smaller number of OH groups by using a mixture of water and the organic solvent. As the result, the following two methods have been found to overcome the difficulty.

One is the method of decreasing the reaction of cyanuric chloride with water by lowering the temperature of the reaction system during the time contacting cyanuric chloride with water when a homogeneous mixture of water and water miscible organic solvent is used. That is, the halogen-containing s-triazine compound (I) is produced by reacting cyanuric chloride, the phenol (II) and the bisphenol (III) at a molar ratio of 1:(3-2a); a ($0<a<3/2$), in the presence of about 3 equivalent of the base in the solvent wherein a homogeneous mixture of water and the organic solvent is used and the temperature of the reaction system is kept at lower than 5° C. preferably lower than 3° C. during the time from dissolving cyanuric chloride in the solvent to the initiation of the treatment with the base. After the initiation of the treatment with the base, the reaction of cyanuric chloride with the halophenol (II) and the bisphenol (III) are faster than the reaction of cyanuric chloride with water, whereby the probability of the reaction of cyanuric chloride with water is small. The increase of number of OH groups in the compound (I) can be prevented by lowering the temperature of the reaction system at lower than 5° C. during said time. After initiating the treatment with the base, the temperature of the reaction system can be raised. In order to increase the reaction velocity, it is preferable to rise the temperature of the reaction system after initiating the treatment with the base. It is also possible to use a catalyst.

The other one is the method of using a phase transferring catalyst is used in a heterogeneous mixture of water and water immiscible solvent or water low miscible solvent. That is, the halogen-containing s-triazine compound (I) is produced by reacting cyanuric chloride, the halophenol (II) and the bisphenol (III) at a molar ratio of 1:(3-2a); a (0<a<3/2), in the presence of about 3 equivalent of the base in the solvent wherein the phase transferring catalyst is used in a heterogeneous mixture of water and water immiscible solvent or a solvent which is substantially immiscible to water.

Cyanuric chloride is dissolved in an organic solvent and the probability of contacting cyanuric chloride with water is small. On the other hand, the phenol (II) and the bisphenol (III) are dissolved in an aqueous solution of the base. Accordingly, when the base is added, the organic solvent phase containing cyanuric chloride and the aqueous solution phase containing the phenol (II) and the bisphenol (III) and the base are separated. The amount of the compounds transferring between the two phases is small whereby the reaction velocity is remarkably low. In order to increase the reaction velocity, it is necessary to use a phase transferring catalyst which promotes the transferring the compounds between the water phase and the organic solvent phase by transferring between them, to increase the reaction velocity. Suitable phase transferring catalysts include quaternary ammonium salts and quaternary phosphonium salts.

The phase transferring mechanism of the phase transferring catalyst and the catalytic mechanism can be considered as follows. The case of the quaternary ammonium salt ($R_4N^+Cl^-$; R:alkyl group or aryl group, aralkyl group etc.) will be described. $R_4N^+Cl^-$ dissolved in the water phase is reacted with

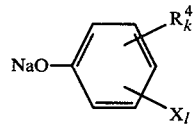

in the water phase to form

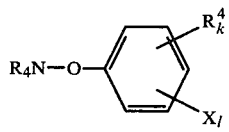

which is soluble in an organic solvent whereby it is transferred into the organic solvent phase. In the organic solvent phase, it is reacted with cyanuric chloride to form $R_4N^+Cl^-$ by the following reaction and $R_4N^+Cl^-$ is transferred into the water phase.

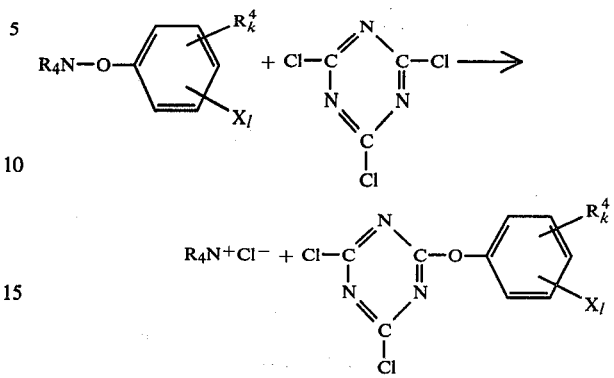

The quaternary ammonium salts should have suitable alkyl group, aryl group or aralkyl group (R).

Suitable quaternary ammonium salts include triethyl benzyl ammonium chloride, methyl tricapryl ammonium chloride, tetrabutyl ammonium bromide, dodecyl trimethyl ammonium chloride, tetrapropyl ammonium chloride, n-hexadecyl tributyl ammonium chloride etc.

Suitable phosphonium salts include n-hexadecyl tributyl phosphonium bromide etc.

Suitable water inmiscible solvents and solvents which are substantially inmiscible to water through aliphatic hydrocarbons, alicyclic hydrocarbons, aromatic hydrocarbons and halogenated compounds thereof. It is especially preferable to use methylenechloride, chloroform, carbon tetrachloride, dichloroethane, trichloroethane, trichloroethylene, perchloroethylene, monochlorobenzene, dichlorobenzene and other halohydrocarbons from the viewpoint of inflammable which is preferable in an industrial operation.

The halogen-containing s-triazine compounds (I) having high molecular weight are easily obtained by the latter process. It is easy to obtain the compound (I) having more than 10 of triazine rings. It is also possible to obtain the compounds (I) having more than 20 of s-triazine rings. The compounds (I) having quite high molecular weight can be also obtained.

The latter process is quite different from the former process using the homogeneous mixture of water and the organic solvent. It is not necessary to maintain the solutions at low temperature during the time dissolving cyanuric chloride in the organic solvent and contacting it with the aqueous solution of the base because the dehydration of the organic solvent can be easily attained and the dehydrated organic solvent can be reused.

The hydrolysis of cyanuric chloride can be prevented by using the organic solvent which does not contain water before initiating the reaction by contacting with the aqueous solution of the base. The phenol (I) and the bisphenol (III) can be dissolved in the organic solvent together with cyanuric chloride. The phenol (II) and the bisphenol (III) can be also dissolved in the aqueous solution of the base and then they can be reacted with cyanuric chloride in the organic solvent.

When the reaction is performed by using the homogeneous mixture of water and the organic solvent or the heterogeneous mixture of water and the organic solvent, the reaction conditions such as temperature and time or the operation of the reaction and the post-treatment can be the same with those of the process using the organic solvent without water. For example, the reaction temperature is preferably lower than 40° C. The reaction is performed with stirring and the aging of the reaction product can be attained by heating the reaction mixture after adding all of the base. The multi-step reaction for reacting them by separately adding the phenol (II) and the bisphenol (III) can be employed.

In these processes, white powdery products can be obtained. In some case, pale yellow color is found by separating halogen. The decoloring is easy. For example, the decoloring can be attained by adding a decoloring agent in a washing solution, or by adding a decoloring agent such as a reducing agent into the reaction system to perform the reaction in the presence of the decoloring agent.

The product is usually dissolved in tetrahydrofuran except the product having quite high molecular weight. The molecular weight can be measured by using the solution. When the products are ones having quite high molecular weight in the chain structure, the net structure or the cyclic structure, there is no solvent for dissolving the product whereby the molecular weights can not be measured and the products are considered to be polymers having infinite molecular weight. The polymers having infinite molecular weight are also effective as flame retardants in the present invention.

The following examples are given for purposes of illustration. It will be understood that the invention is not limited to these examples.

In the examples, the compounds are designated by the following references.

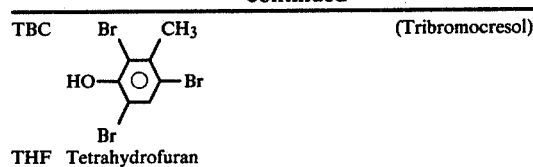

TBC (Tribromocresol)

THF Tetrahydrofuran

The test methods in the examples are as follows:

Bromine content: Fluorescent X-ray

Analyzer (KGX: manufactured by Rigaku Denki K.K.) was used to measure intensity of $K_\alpha$ rays of Br. (THF solution was used).

Number average molecular weight:

It was measured by the vapor pressure osmosis using THF solution.

Average number of OH groups per one molecule:

It was measured by the neutralization titration (Phenolphthalein indicator) with KOH ethanol solution. In this case, all of acidic groups of the products may be OH groups bonded on benzene rings.

Thermal decomposition initiating temperature:

It was measured by using the apparatus TG-DTA standard type manufactured by Rikagaku Denki K.K. at a temperature rising speed of 10° C./hour in air flow.

UL-94:

It was measured by the test of Underwriter's Laboratories, Inc. Bulletin UL-94. The test piece having a size of ⅛ inch×½ inch×5 inch was used. The rating of flammability is in order of HB, V-2, V-1, V-0.

Tensile strength:

It was measured under ASTM D638.

Thermal deforming temperature:

It was measured under ASTM D648 (18.6 Kg/cm$^2$).

Preparation of halogen-containing s-triazing compounds:

A. Solvent: only organic solvent

EXAMPLE 1:

In 200 ml four necked glass flask equipped with a reflux condenser, a thermometer, a dropping funnel and a mechanical stirrer, 13.60 g (0.025 mole) of TBA, 33.60 g (0.10 mole) of TBP and 9.22 g (0.05 mole) of cyanuric chloride were charged, and 100 g of THF was further charged. The mixture was stirred and cooled to 5° C., and 12.48 g of 50 wt.% of aqueous solution of NaOH was added dropwise through the dropping funnel under maintaining the temperature of the reaction mixture at lower than 10° C. After the addition, the reaction mixture was maintained at lower than 10° C. for 30 min. and then was heated at a rate of 10° C./hour to the refluxing temperature. The reaction mixture was maintained at the refluxing temperature for 3 hours and then it was filtered and was mixed with 2 liters of methanol to precipitate the product. The precipitate was sequentially washed with 0.1 N-HCl, 1 liter of water and 2 liters of methanol and then was dried to obtain 47.45 g of the white powder having the bromine content of 64.0%, the number average molecular weight of 2,800, the average number of OH groups per 1 molecule of 0.04 and the thermal decomposition initiating temperature of 351° C.

EXAMPLES 2 TO 9

In accordance with the process of Example 1 except varying the starting materials, the amounts and the ratio thereof, halogen-containing s-triazine compounds have been produced. The results are shown in Table 1.

ping funnel under maintaining the temperature of the reaction mixture to lower than 10° C. After the addition, the reaction mixture was treated by the process of Example 1 to obtain 47.05 g of a white powder having the bromine content of 63.9%, the number average molecular weight of 2300, the average number of OH groups per 1 molecule of 0.02 and the thermal decomposition initiating temperature of 328° C.

Table 1

| Exp. No. | Starting materials and amounts | | | | Products | | | |
|---|---|---|---|---|---|---|---|---|
| | cyanuric chloride g (mole) | bisphenol g (mole) | halo-phenol g (mole) | 50 wt. % NaOH aq. g (mole) | Yield g | *1 Hal. content % | *2 M.W. | *3 OH groups |
| 2 | 9.22 (0.05) | TBA 21.76 (0.04) | TBP 23.16 (0.07) | 12.96 (0.162) | 44.87 | 59 | 4,500 | 0.11 |
| 3 | 4.61 (0.025) | TBA 12.24 (0.0225) | TBP 9.93 (0.03) | 6.24 (0.078) | 22.46 | 60.1 | 9,200 | 0.20 |
| 4 | 3.69 (0.02) | TBS 5.66 (0.01) | TBP 13.23 (0.04) | 4.96 (0.062) | 18.96 | 61.5 | 1,900 | 0.19 |
| 5 | 9.22 (0.05) | BPA 5.71 (0.025) | TBP 33.60 (0.10) | 12.48 (0.156) | 39.13 | 55.9 | 1,750 | 0.02 |
| 6 | 9.22 (0.05) | TCA 14.64 (0.04) | TBP 23.16 (0.07) | 12.96 (0.162) | 38.64 | 54.0 *4 (40.5) | 3,900 | 0.09 |
| 7 | 9.22 (0.05) | TBA 13.60 (0.025) | PBP 12.22 (0.025) TBP 24.81 (0.075) | 12.48 (0.156) | 44.75 | 64.0 | 1,900 | 0.23 |
| 8 | 9.22 (0.05) | TCA 16.47 (0.045) | TCP 13.65 (0.06) | 12.96 (0.162) | 29.94 | 37.4 | 6,200 | 0.25 |
| 9 | 9.22 (0.05) | TBA 21.76 (0.04) | TBC 24.14 (0.07) | 12.96 (0.162) | 46.4 | 59.2 | 5,100 | 0.06 |

*1 halogen content
*2 number average molecular weight
*3 average number of OH groups per one molecule
*4 ( ) bromine content

B. Solvent: Homogeneous mixture of water and organic solvent

Reference 1

After completing the reaction in the process of Example 1, the mixture of THF and water was distilled. The resulting azeotropic mixture of THF and water was a homogeneous mixture containing 94 wt. parts of THF and 6 wt. parts of water. In accordance with the process of Example 1 except using 100 g of the homogeneous mixture instead of 100 g of THF, the reaction was carried out to obtain 39.5 g of a white powder having the bromine content of 61.3%, the number average molecular weight of 1,500, the average number of OH groups per 1 molecule of 0.88 and the thermal decomposition initiating temperature of 158° C.

EXAMPLE 10

In the 200 ml four necked glass flask of Example 1, 13.60 g (0.025 mole) of TBA and 33.60 g (0.10 mole) of TBP were charged at 20° C., and 94 g of THF and 6 g of water were added. The mixture was stirred and cooled to 0° C., and 9.22 g (0.05 mole) of cyanuric chloride was added with stirring to form the homogeneous mixture, and 12.48 g (0.156 mole) of 50 wt.% NaOH aqueous solution was added dropwise through the drop-

EXAMPLE 11

In the 200 ml four necked glass flask of Example 1, 21.76 g (0.04 mole) of TBA was charged at 20° C. and 56.4 g of THF and 3.60 g of water was added with stirring to cool it at 0° C. and 9.22 g (0.05 mole) of cyanuric chloride was added with stirring to form a homogeneous solution. Then, 6.40 g (0.08 mole) of 50 wt.% of NaOH aqueous solution was added dropwise through the dropping funnel under maintaining the temperature of the reaction mixture at lower than 10° C. After the addition, the mixture was stirred at lower than 10° C. for 30 minutes. Then, a solution prepared by dissolving 23.16 g (0.07 mole) of TBP in a mixture of 37.6 g of THF and 2.40 g of water was added to the reaction mixture. Then, 6.00 g (0.075 mole) of 50 wt.% NaOH aqueous solution was added dropwise through the dropping funnel under maintaining the temperature of the reaction mixture at lower than 10° C. After the addition, the reaction mixture was maintained at lower than 10° C. for 30 minutes and then, it was raised at a rate of 10° C./hour to the refluxing temperature. The reaction mixture was maintained at the refluxing temperature for 3 hours and was cooled and filtered. The filtrate was added to a mixture of 500 g of isopropyl alcohol and 68 g of water to form precipitate. The precipitate was filtered and sequentially washed with said mixture and water and was dried to obtain 45.12 g of a white powder having 60.60% of the bromine content, the number average molecular weight of 4800, the average number of OH groups per one molecule of 0.03 and the thermal decomposition initiating temperature of 331° C.

EXAMPLE 12

In 300 ml four necked glass flask similar to that of Example 1, 16.47 g (0.045 mole) of TCA, and 13.65 g (0.060 mole) of TCP were charged at 20° C., and 94 g of THF and 6 g of water were added with stirring under cooling at 0° C. At the temperature, 9.22 g (0.05 mole) of cyanuric chloride was added with stirring to form a homogeneous solution. Then, 12.48 g (0.156 mole) of 50 wt.% NaOH aqueous solution was added dropwise through the dropping funnel under maintaining the temperature at 10° C. After the addition, the temperature of the reaction mixture was maintained at 10° C. for 30 minutes and then was raised at a rate of 10° C./hour to the refluxing temperature. The reaction mixture was maintained at the refluxing temperature for 3 hours and was cooled and filtered. The filtrate was mixed with 2 liters of methanol to precipitate the product. The precipitate was sequentially washed with 200 ml of 0.1 N-HCl, 1 liter of water and 200 ml of methanol and was dried to obtain 28.35 g of a white powder having the chlorine content of 37.9%, the number average molecular weight of 6100, the average number of OH groups per 1 molecule of 0.13 and the thermal decomposition initiating temperature of 322° C.

C. Solvent: Heterogeneous mixture of water and organic solvent

EXAMPLE 13

In the 200 ml four necked glass flask of Example 1, 0.20 g (0.00045 mole) of methyltricapryl ammonium chloride (ALIQVAT-336 manufactured by General Mills Co.), 29.77 g (0.09 mole) of TBP and 5.53 g (0.03 mole) of cyanuric chloride were dissolved in 80 g of dehydrated 1,1,1-trichloroethane and the mixture was cooled at 0° C. Then, 39.6 g (0.099 mole) of 10 wt.% of NaOH aqueous solution was added dropwise under maintaining the temperature to lower than 10° C. After the addition, the temperature of the reaction mixture was maintained at lower than 10° C. for 30 minutes and then, was raised at a rate of 20° C./hour to the refluxing temperature and the refluxing temperature was maintained for 1 hour. Then, 1,1,1-trichloroethane was distilled off and the mixture of the solid and the aqueous solution was discharged and the solid was pulverized by the conventional method and 1.0 g (0.025 mole) of NaOH was added to dissolve the unreacted material in the aqueous solution and the product was filtered and the precipitate was sequentially washed with 100 g of water, 100 g of 0.1 N-HCl, 100 g of water and 50 g of n-hexane and was dried to obtain 29.76 g of a white powder having the bromine content of 66.5%, the number average molecular weight of 1050, the average number of OH groups per 1 molecule of 0.0003. The thermal decomposition temperature was not clear because it was sublimated at 280° C. though it was stable to 280° C.

EXAMPLE 14

In the 200 ml four necked glass flask of Example 1, 0.1 g (0.00045 mole) of triethyl benzyl ammonium chloride, 10.88 g (0.02 mole) of TBA, 16.54 g (0.05 mole) of TBP, 3.60 g (0.09 mole) of NaOH and 100 g of water were charged and the mixture was stirred at 25° C. to dissolve them as substantial homogeneous solution. Then, a solution of 5.53 g (0.03 mole) of cyanuric chloride in 80 g of methylene chloride was added to the solution with stirring. The mixture was stirred at the refluxing temperature of 40° C. for 2 hours.

In accordance with the process of Example 13, methylene chloride was removed and the product was purified to obtain 28.10 g of a white powder having the bromine content of 60.13%, the number average molecular weight of 5100, the average number of OH groups per 1 molecule of 0.12 and the thermal decomposition initiating temperature of 310° C.

EXAMPLE 15

In the 200 ml four necked glass flask of Example 1, 0.1 g (0.00045 mole) of triethyl benzyl ammonium chloride, 5.53 g (0.03 mole) of cyanuric chloride were dissolved in 80 g of methylene chloride and the mixture was stirred at 25° C. Then, a solution of 10.88 g (0.02 mole) of TBA, 1.62 g of NaOH and 0.05 g of NaHSO$_3$ in 50 g of water was added to the solution and the mixture was stirred at 25° C. for 1 hour. Then, a solution of 16.54 g (0.05 mole) of TBP and 2.02 g (0.0505 mole) of NaOH in 50 g of water was added to the mixture. The reaction mixture was stirred at 25° C. for 1 hour and then, at the refluxing temperature of 40° C. for 3 hours. Then, methylene chloride was distilled off and the mixture of the solid and water was discharged and the solid was pulverized and 1.0 g (0.025 mole) of NaOH was added to dissolve the unreacted material in water and the product was filtered. The precipitate was sequentially washed with 100 g of water, 100 g of 0.1 N-HCl, 500 g of water and 50 g of methanol and was dried to obtain 27.96 g of a white powder having the bromine content of 60.22%, the number average molecular weight of 3010, the average number of OH groups per 1 mole of 0.37 and the thermal decomposition initiating temperature of 301° C.

EXAMPLE 16

In 300 ml four necked glass flask, similar to that of Example 1, 16.54 g (0.05 mole) of TBP, 11.32 g (0.02 mole) of TBS, 3.96 g (0.099 mole) of NaOH, 0.05 g of NaHSO$_3$ and 100 g of water were charged and the mixture was stirred to form the substantial homogeneous solution. Then, a solution of 5.53 g (0.03 mole) of cyanuric chloride and 0.40 g (0.0009 mole) of methyl tricapryl ammonium chloride, in 100 g of o-dichlorobenzene was added to the solution at lower than 30° C. Then, the reaction mixture was stirred and the temperature was raised at a rate of 20° C./hour to the refluxing temperature and the refluxing temperature was maintained for 5 hours. Then, 1.0 g (0.025 mole) of NaOH was added and o-dichlorobenzene was distilled off under bubbling steam. The solid and water was discharged and the solid was pulverized and the product was filtered. The precipitate was sequentially washed with 100 g of water, 100 g of 0.1 N-HCl, 500 g of water and 100 g of methanol and was dried to obtain 28.29 g of a white powder having the bromine content of 63.75%, the number average molecular weight of 2930, the average number of OH groups per 1 molecule of 0.34 and the thermal decomposition initiating temperature of 308° C.

Effect of halogen-containing s-triazine compound as flame retardant

EXAMPLE 17

The flame retardancies of the halogen-containing s-triazine compounds prepared by the examples to synthetic resins were tested.

The commercial thermoplastic resins, the halogen-containing s-triazine compounds (shown by Example No.) and the auxiliary agent ($Sb_2O_3$) were blended to form the compositions shown in Table 2, and the compositions were respectively kneaded by an extrusion molding machine in the conventional condition to form pellets, and were respectively molded by the injection molding machine to form test pieces having size of $\frac{1}{8}$ inch×$\frac{1}{2}$ inch×5 inch. The test pieces were tested in accordance with the test method of UL-94.

As the reference, the test pieces prepared by combining no halogen-containing s-triazine compound or no auxiliary agent, were also tested.

In the case of the epoxy resin in the test No. 11 and No. 12, the components in Table 2 were mixed and kneaded by a roll mill and the compositions were molded in vacuum to form the plate having size of $\frac{1}{8}$ inch×10 inch×6 inch, and were cured at 120° C. for 2 hours and were further heated at 200° C. for 2 hours. Test pieces having size of $\frac{1}{8}$ inch×$\frac{1}{2}$ inch×5 inch were cut out from the plate and were tested in accordance with the test method of UL-94. The results are shown in Table 2.

The tensile strength and the thermal deformation temperature of the test pieces of the thermoplastic resins containing the flame retardant were measured in accordance with ASTM. The results are also shown in Table 2. The test pieces had white color and had not coloring nor bleed-out.

What is claimed is:

1. A flame retardant which comprises a halogen-containing s-triazine compound having the formula

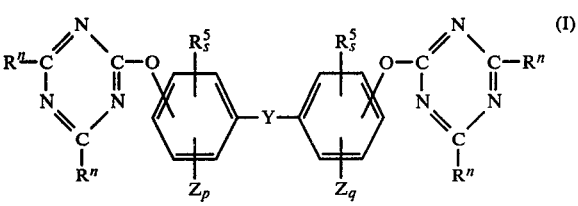

wherein $R^n$ is OH, $R^1$, $R^2$ or $R^3$;

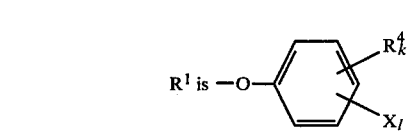

wherein:
$R^4$ is a lower alkyl group or a lower haloalkyl group;
X is Br or Cl
k, l=0 or an integer of 1 to 5;
k+l≦5

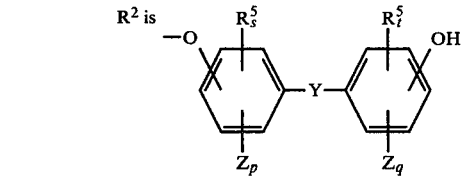

wherein
$R^5$ is a lower alkyl group or a lower haloalkyl group:

Table 2

| Test No. | Synthetic resin | Halogen-containing s-triazine compound | Auxiliary agent ($Sb_2O_3$) | UL-94 | Tensile strength (Kg/cm$^2$) | Thermal deform. temp. (°C.) |
|---|---|---|---|---|---|---|
| 1 | polystyrene 79.7 | Example 1 16.3 | 4.0 | V-0 | 278 | 83 |
| 2 | polystyrene 78.3 | Example 2 17.7 | 4.0 | V-0 | 301 | 84 |
| 3 | polystyrene 78.5 | Example 3 17.4 | 4.0 | V-0 | 288 | 85 |
| 4 | polystyrene 100 | — | — | HB | 340 | 82 |
| 5 | ABS 76.2 | Example 4 19.8 | 4.0 | V-0 | 325 | 86 |
| 6 | ABS 100 | — | — | HB | 370 | 82 |
| 7 | polypropylene 87.5 | Example 5 9.5 | 3.0 | V-2 | 280 | 71 |
| 8 | polypropylene 100 | — | — | HB | 345 | 67 |
| 9 | polybutyrene terephthalate 76.5 | Example 6 19.5 | 4.0 | V-2 | 505 | 68 |
| 10 | polybutyrene terephthalate 100 | — | — | HB | 620 | 60 |
| 11 | Epoxy resin 50 Hardener 40 (HHPA) Hardener 0.5 (dimethyl benzylamine) | Example 2 15.0 | 3.8 | V-0 | — | — |
| 12 | same with No. 11 | — | — | HB | — | — |

Z is Br or Cl

Y is a lower alkylene, a lower haloalkylene group, or —SO$_2$, —SO—, —S—, —O—, —CO— or direct bond R$^3$ is

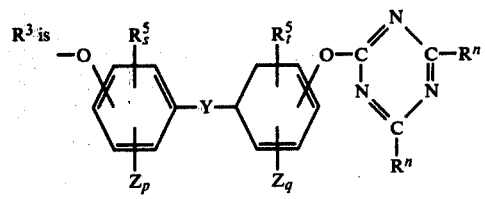

wherein R$^n$, R$^5$, Z, Y, are as defined above; and throughout p, q=0 or an integer from 1 to 4;

s, t=0 or an integer from 1 to 4;

p+q+s+t≦8

1+p+q≧2.

2. The flame retardant of claim 1 wherein said halogen-containing s-triazine compound comprises 2 to 20 s-triazine rings.

3. The flame retardant of claim 1 wherein in said halogen-containing s-triazine compound comprises an average number of OH groups less than 0.5 per molecule.

4. The flame retardant of claim 1 wherein in said halogen-containing s-triazine compound k=0 in R$^1$.

5. The flame retardant of claim 1 wherein in said halogen-containing s-triazine compound s=t=0 in R$^2$ and R$^3$ and Y is a lower alkylene group or —SO$_2$—.

6. The flame retardant of claim 1 wherein in said halogen-containing s-triazine compound 1+p+q≧5 in R$^1$ and R$^2$.

* * * * *